United States Patent [19]

Ahmed et al.

[11] Patent Number: 5,147,047
[45] Date of Patent: Sep. 15, 1992

[54] PELLET INSPECTION SYSTEM

[75] Inventors: Hassan J. Ahmed, Irmo, S.C.; John M. Beatty, Murrysville; Ralph W. Kugler, Mt. Lebanon Township, Allegheny County, both of Pa.

[73] Assignee: Westinghouse Electric Corp., Pittsburgh, Pa.

[21] Appl. No.: 640,770

[22] Filed: Jan. 14, 1991

[51] Int. Cl.$^5$ .............................................. B07C 5/02
[52] U.S. Cl. .................... 209/538; 198/721; 209/586; 209/917; 209/934; 209/939; 356/426; 376/261; 414/433
[58] Field of Search ............... 209/538, 540, 576, 577, 209/586, 587, 939, 917, 934, 517, 539; 376/261; 198/721; 414/433, 222; 356/398, 237, 426; 358/106; 382/1, 8

[56] References Cited

U.S. PATENT DOCUMENTS

| | | | |
|---|---|---|---|
| 2,717,548 | 9/1955 | Blair, Jr. ......................... | 198/721 X |
| 3,260,364 | 7/1966 | England ......................... | 209/673 X |
| 3,355,014 | 11/1967 | Howels ......................... | 209/538 |
| 4,103,776 | 8/1978 | Taniguchi et al. . | |
| 4,138,821 | 2/1979 | Wilks ......................... | 33/174 Q |
| 4,349,112 | 9/1982 | Wilks et al. ................... | 209/538 |
| 4,377,238 | 3/1983 | Wilks et al. ................... | 209/587 |
| 4,448,680 | 5/1984 | Wilks et al. ................... | 209/579 |
| 4,468,163 | 8/1984 | King et al. ..................... | 376/261 X |
| 4,496,056 | 1/1985 | Schoenig, Jr. et al. .......... | 209/539 |
| 4,532,723 | 8/1985 | Kellie et al. ..................... | 376/261 X |
| 4,549,662 | 10/1985 | Schoenig, Jr. et al. .......... | 209/539 |
| 5,019,326 | 5/1991 | Yaginuma et al. ............... | 376/261 |

FOREIGN PATENT DOCUMENTS 2057675 4/1981 United Kingdom ............... 356/426

*Primary Examiner*—Donald T. Hajec

[57] ABSTRACT

A method and apparatus for inspecting cylindrically configured pellets for surface defects is disclosed. At least one axially extending linear portion of the peripheral surface of the pellet is optically sensed. A set of discrete digital values representative of the optically sensed linear portion of the pellet surface is generated and the set of digital values is compared to a predetermined standard. Groups of digital values representative of adjacent locations on the surface of the pellet having values greater or less than the predetermined standard are identified. The area of adjacent digital values having a value above the standard, and the area of adjacent digital values having a value below the standard are calculated and compared to a predetermined area. The pellet is rejected when the calculated area exceeds a predetermined area. During inspection, the pellet is moved axially through an inspection station by first and second horizontally positioned substantially parallel and longitudinally extending pellet support rolls. The rolls are spaced a distance from each other less than the diameter of a pellet to be transferred. The rolls are rotated upward and outward from each other and chain dogs are positioned between the spaced rolls for engaging a pellet and moving the pellet along between the spaced pellet support rolls.

26 Claims, 5 Drawing Sheets

PELLET INSPECTION SYSTEM

BACKGROUND OF THE INVENTION

This invention relates to a method and apparatus for inspecting cylindrically configured pellets for surface defects.

In the manufacture of nuclear fuel rods, nuclear fuel pellets, which are formed from a matrix of enriched or natural uranium oxide, are inserted into elongated, hollow rods typically formed from an alloy of zirconium.

The rods are sealed at the end with end plugs and the rods are pressurized. The rods are stacked in an array to from the core of a nuclear fuel reactor. Defects in the pellets, such as fissures or cracks, often produce chips during reactor operation which can adversely affect the nuclear fuel reactor operation. For example, during reactor operation, a loose chip dislodged from a nuclear fuel pellet could become lodged within the fuel rod adjacent the interior wall of the rod. During reactor operation, the fissionable material contained in the dislodged chip will continue its fissionable reaction and the heat generated during fission may create a defined area of intense heat on the rod wall. As a result, this localized area of intense heat will weaken the rod at the localized point and may cause a rupture in the rod wall creating a leak of the high pressure gas in the rod. If this occurs, the reactor core may have to be shut down Additionally, other pellet surface defects, such as the inclusion of metal in the pellet surface, are objectionable because the defects adversely affect the normal fission reaction of the uranium. As a result, fuel pellets must be inspected during their manufacture for unacceptable surface defects. Preferably, a pellet visual inspection process will have almost one hundred percent inspection validity for assuring defect free production of fuel rods.

In some nuclear fuel manufacturing plants, fuel pellets are manually inspected. Specially dressed inspectors view a single side of a tray of pellets. The pellets are stacked in the tray lengthwise. The tray is positioned under a light source for illuminating the pellets. The pellets are stacked end-to-end and the pellet-to-pellet interface is highlighted to facilitate the inspectors' locating of end defects and surface irregularities.

After one side of a tray is viewed, a lid is placed over the tray of pellets, and the tray inverted. The backside of the tray is removed to yield viewing access to the opposite side of the pellets. The inspector completes the inspection process by viewing the pellets as before.

This type of manual inspection suffers several drawbacks. Radioactive and hazardous dust often is present in the air. The inspectors must be protected against this dust with special protective clothing. Additionally, the prolonged visual inspection of the trays is inherently strenuous to the eyes which causes inspector error over prolonged periods of time. Also, uranium pellets are heavy and the continual inverting of the trays containing the pellets is tiresome to the inspector.

As a result of the danger involved in a manual pellet inspection system, it is more desirable to automatically inspect nuclear fuel pellets without relying on human involvement. Many automated pellet inspection systems, however, have suffered several drawbacks. Nuclear fuel pellets are extremely abrasive, and the pellet engaging surfaces of material handling systems tend to wear quickly. Additionally, if small chips are broken from off a nuclear fuel pellet during handling, they often damage the belts, rollers and gears of the material handling systems.

In one automated prior art pellet inspection apparatus, pellets are stacked end-to-end and illuminated and the interface between the pellets analyzed by appropriate optics and cameras. The stacking of pellets is undesirable because the interface between two contiguous pellets must be determined to distinguish between pellets. If the individual pellets vary in length from each other, the only method for separating individual pellets for inspection analysis is by finding the edge-to-edge interface and then segregating among the individual pellets. At the same time the edge-to-edge interface is determined, complete inspection of the pellet surface must occur and if a pellet is determined defective, the edge-to-edge interface often must be detected again to identify and reject the defective pellet. This type of system is complex. Additionally, because the pellets are stacked during inspection, complex material handling equipment is necessary to ensure proper feeding and stacking of pellets during conveyance and inspection. An example of such an automatic pellet inspection system as described above is disclosed in U.S. Pat. No. 4,496,056 to Schoenig, Jr. et al. As described therein, individual nuclear fuel pellets are conveyed in stacked relationship to each other to a pellet inspection area. The interface between the stacked pellets is located and the surface reflectivity of the pellets is analyzed to determine the cylindrical shape and length of the pellet. As is described in related U.S. Pat. No. 4,549,662 to Schoenig et al., the disclosed apparatus for effecting the inspection process is complex for ensuring the proper conveyance and delivery of a stack of pellets.

In another complex pellet inspection apparatus, disclosed in the U.S. Pat. No. 4,448,680 to Wilks et al., a nuclear fuel pellet is transferred to an array of stations for detecting at individual stations the diameter, length and surface flaws on the pellet. At the surface flaw detection station, a converging beam is cast on a fuel pellet by a rotating scanning prism. Flaws are detected by detecting alternating light and dark areas. However, this type of system does not provide for reliable analysis of defects such as metal inclusions which typically are visualized as brighter spots on the pellet surface than the surrounding pellet surface. Additionally, the system requires complex pellet handling systems.

SUMMARY OF THE INVENTION

The apparatus and method of the present invention inspects cylindrically configured pellets for surface defects. In the method and apparatus of the present invention, at least one axially extending linear portion of the peripheral surface of the pellet is optically sensed. A set of discrete digital values representative of the optically sensed portion of the pellet surface is generated. The set of digital values is compared to a predetermined standard to identify groups of digital values representative of adjacent locations on the surface of the pellet having values greater or less than the predetermined standard. The entire peripheral surface of the pellet is sensed as a series of sets of discrete digital values representative of different axially extending portions of the surface of the pellet. An image of the pellet is formed. Preferably, the predetermined standard is a range of digital values having an upper limit defining an upper threshold and a lower limit defining a lower threshold. The values below the lower limit are processed as darker surface defects such as cracks and chips. The values above the upper limit are processed as metal inclusions.

During inspection the pellet is rotated and optically sensed in timed sequence to obtain the series of sets of discrete digital values. During sensing, the pellet is moved axially through an inspection station. The area of adjacent digital values which have a value less than the predetermined standard is calculated and the pellet rejected when the calculated area is greater than a predetermined area. Additionally, the area of adjacent digital values having a value greater than the predetermined standard is calculated and a pellet rejected when the area is greater than a predetermined area.

Control means includes receiving means for receiving signals from the line scan camera means representative of the surface of the pellet. Comparing means compares the signals received from the line scan camera means and identifies groups of digital values representative of adjacent locations on the surface of the pellet having values greater or less than the predetermined standard. Reject means is responsive to the control means for rejecting a pellet after a pellet is determined defective.

Edge analysis for defects is performed by sensing the entire peripheral surface of the pellet as a series of sets of discrete digital values, forming an image of the pellet as noted before, and identifying digital values corresponding to the edges of the pellet. The area circumscribed by the edges of the pellet is calculated. The pellet is rejected if the calculated value is greater than a predetermined amount.

Initially, before inspecting an unknown fuel pellet, the apparatus is calibrated by optically sensing the peripheral surface of a known pellet and generating a two dimensional digital image having a two dimensional array of digital values representative of the optically sensed surface of the known pellet. An average value for the array of digital values in the first two dimensional digital image is determined. The average value is used for establishing the predetermined standard. The set of digital values of an unknown then are compared to the predetermined standard.

The apparatus includes line scan camera means position to scan axially the pellet surface at an inspection station, and means for axially transporting a pellet through the inspection station while rotating the pellet along its longitudinal axis. The transport and rotation means includes first and second horizontally positioned substantially parallel and longitudinally extending pellet support rolls. The rolls are transversely spaced a distance from each less than the diameter of a pellet to be transferred. This spaced distance assures that a pellet will be supported on the two pellet support rolls without falling between the rolls. Drive means is connected to the pellet support rolls for rotating the pellet support rolls upward and outward from each other. Means is positioned between the spaced rolls for engaging the pellet and moving the pellet between the pellet support rolls. The moving means positioned between the transversely spaced pellet support rolls for engaging and moving a pellet includes a longitudinally extending endless loop pellet transport chain positioned adjacent and below one of the pellet support rolls. The pellet transport chain includes a plurality of spaced, laterally extending arms having dog thereon. The endless loop pellet transport chain is positioned so that during movement of the chain, the dogs are moved between the rolls and longitudinally therebetween for engaging and moving a pellet supported thereon. The apparatus also includes a pellet discharge area having a downwardly extending chute positioned adjacent the end of the pellet support rolls for receiving a pellet from the rolls. Reject means comprises means positioned adjacent said chute for pushing a pellet transversely from off said chute.

BRIEF DESCRIPTION OF THE DRAWINGS

Some of the objects and advantages of present invention having been stated, others will appear as the description proceeds, when taken in conjunction with the accompanying drawings, in which:

FIG. 1-A is a schematic representation of the directional rotation of the pellet support rolls;

DETAILED DESCRIPTION

Figures 1, 1A:
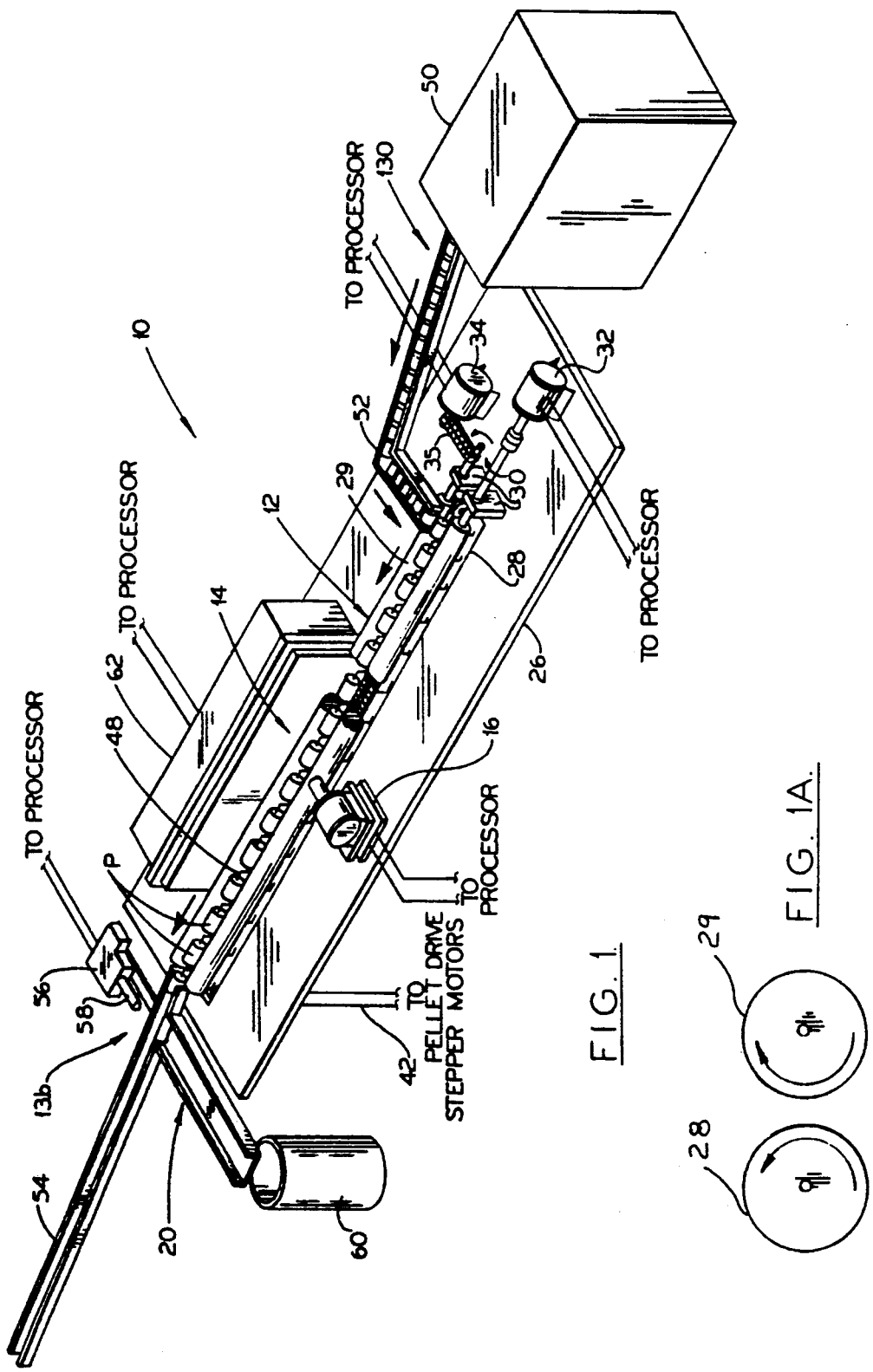
FIG. 1 is a schematic, isometric view of the pellet transport system in accordance with the present invention.
Figure 2:
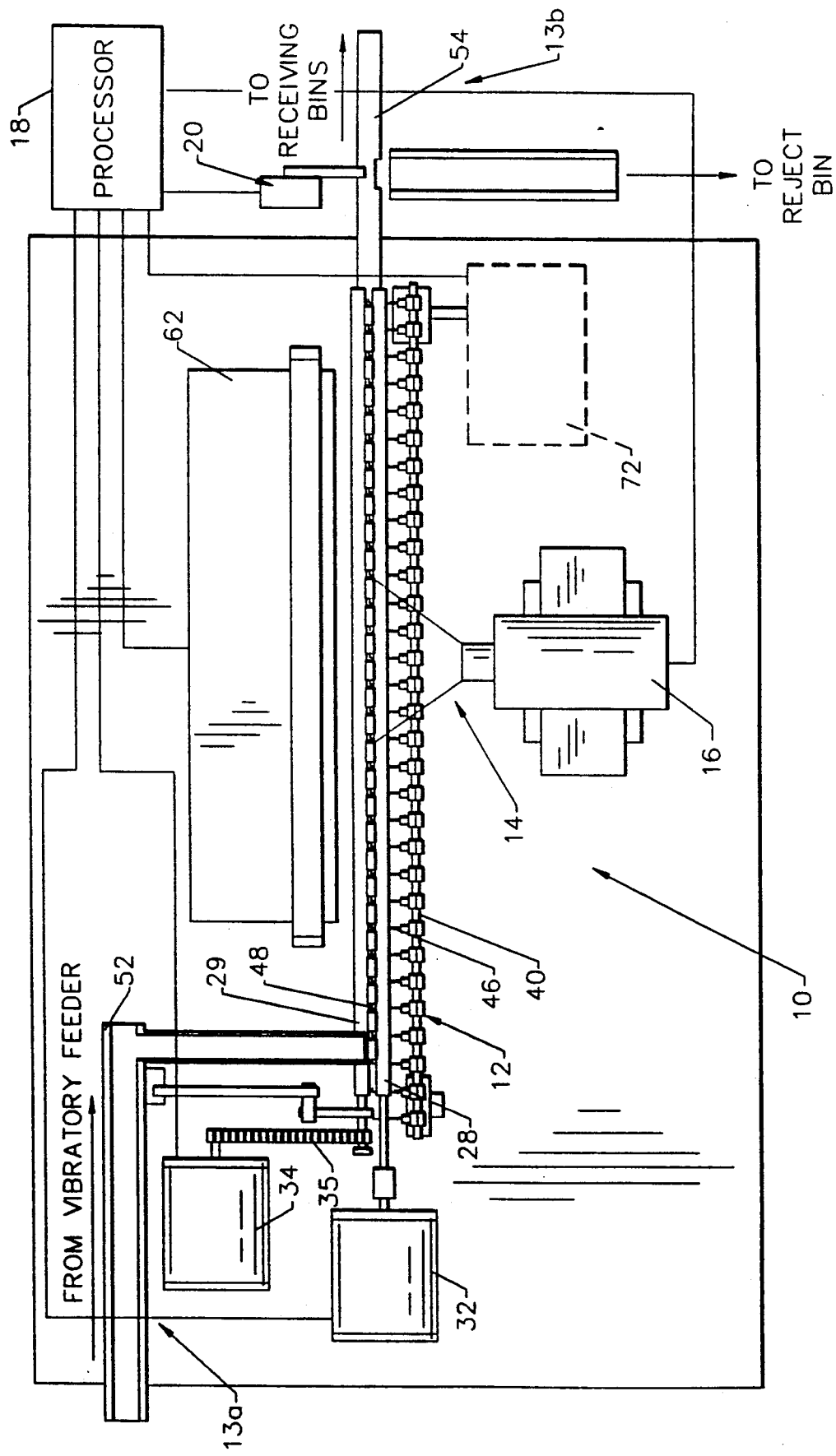
FIG. 2 is a plan view of the pellet transport system in accordance with the present invention and showing the positional relationship of various components relative to the pellet support rolls.
Figure 3:
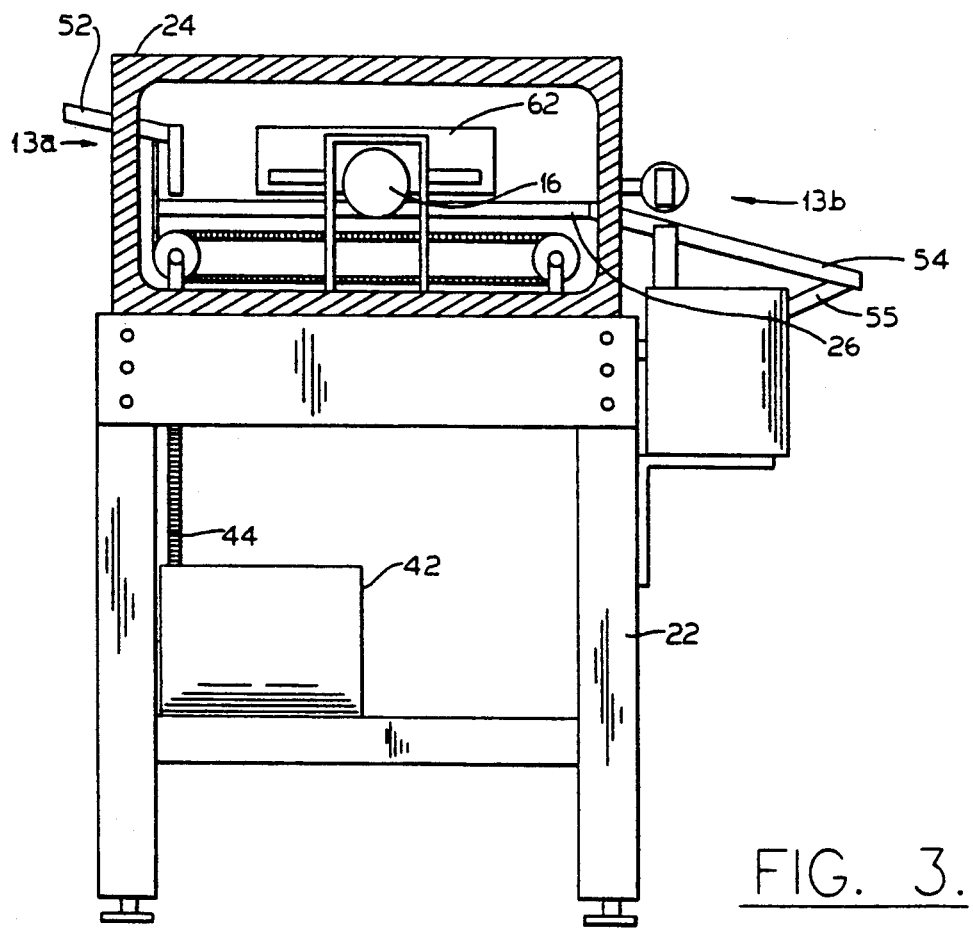
FIG. 3 is a side, elevation view of the pellet transport system and the housing and frame supporting same.

Referring now to FIGS. 1-3, there is illustrated the apparatus 10 for inspecting cylindrically configured pellets P, illustrated as nuclear fuel pellets, for surface defects. The apparatus broadly includes transport means indicated generally at 12 for rotating along its longitudinal axis and axially transporting nuclear fuel pellets P along a predetermined path of travel from a pellet feed area indicated generally at 13a, through an inspection station, indicated generally at 14, to a pellet discharge area indicated generally at 13b. A line scan camera 16 is positioned adjacent the inspection station 14 and scans axially the pellets' surfaces. Control means in the form of a processor, indicated generally at 18, includes receiving means for receiving signals from the line scan camera 16 representative of the surface of the pellet and comparator means for comparing signals received from the line scan camera and identifying groups of digital values representative of adjacent locations on the surface of the pellet having values greater or less than a predetermined standard (FIG. 2). Reject means, indicated generally at 20, is positioned at the pellet discharge area 13b and is responsive to the processor 18 for rejecting defective pellets.

Although the apparatus and method in accordance with the present invention can be applied to inspecting a large variety of different pellets, the description will proceed by describing the preferred inspection of nuclear fuel pellets. Nuclear fuel pellets P typically are formed of two types of material, i.e. enriched uranium oxide or natural re cylindrical in shape and have diameters ranging between 0.30 inches to 0.40 inches. Their length typically varies between 0.3 inches to 0.6 inches. Their weight varies from about 0.01 to 0.03 pounds.

Various pellet defects are unacceptable because they can adversely affect a nuclear reactor operation. For example, during reactor operation, hairline cracks can enlarge creating a chip which later dislodges from the pellet. The chip can lodge itself against the interior surface of the fuel rod and create an area of intense heat. This weakens the rod at that point which could result in rod failure. Some of the pellet defects to be detected in accordance with the present invention, as will be explained later, include end chips, side chips and fissures (cracks). Many of these defects typically occur during process handling of the pellets. Fissures can be defined as surface cracks which have a width dimension (circumferential) of at least 10 mils and a length of least 10 times the width dimension. Longitudinal fissures extend at an angle greater than 30 degrees to the plane of the pellet end face.

As illustrated in FIG. 1, the pellet transport means is enclosed in a housing 24 which, in turn is positioned on a support frame 22 (FIG. 3). The housing 24 offers some protection to an operator from the uranium dust and other contaminates generated during fuel pellet transport and inspection. The pellet transport means 12 includes a main support table 26 positioned in the housing 24. First and second horizontally positioned substantially parallel and longitudinally extending pellet support rolls 28, 29 are positioned on the main support table 26 and rotatably supported thereon by bearing mounts 30. The pellet support rolls 28, 29 are transversely spaced a distance from each other less than the diameter of the pellet to be transferred to assure that a pellet can rest between the two rolls as illustrated in FIG. 1. Because the fuel pellets P are very abrasive and prone to generate a certain amount of dust, the pellet support rolls 28, 29 and other handling components are formed from a durable material. Preferably, the rolls 28, 29 are fabricated from 440 hardened stainless steel to minimize surface wear. The rolls 28, 29 preferably are 0.625 inches in diameter and from 24–30 inches long.

The first pellet support roll 28 is driven by a first roll drive motor 32 connected axially with the roll. (FIG. 2) A second roll drive motor 34 is positioned offset from the second pellet support roll 29 and includes a transmission support roll drive chain 35 interconnecting the motor shaft and end of the pellet support roll 29. Both motors 32, 34 preferably are stepper motors controlled by the processor 18. As illustrated, the pellet support rolls 28, 29 are substantially equal in length with each other and define a portion of the predetermined path of travel from the pellet feed area 13a to the pellet discharge area 13b.

During operation, both rolls 28, 29 are driven upward and outward from each other (FIG. 1-A) to impart an upward force to the pellet to prevent the possibility that chips dislodged from a pellet will be forced downward between the rolls and into the other components of the pellet transport apparatus. Additionally, one roll 28, 29 is driven at twice the speed of the other roll to provide a net rotation to a pellet during transport. Additionally, because pellets are transferred on the rolls throughout the length of the rolls and the rolls rotate, wear on the rolls 28, 29 is uniform.

The pellet transport 12 for moving the pellets axially along the path of travel through the inspection station 14 includes a longitudinally extending endless loop pellet transport chain 40 positioned adjacent to and slightly below the first pellet support roll 28 (FIG. 2). The pellet transport chain 40 preferably is formed of stainless steel having 0.375 inch pitch links. As illustrated the pellet transport chain 40 is offset from directly under the pellet path of travel of the rolls 28, 29 to avoid contamination from pellet dust and fallen chips. A pellet drive stepper motor 42 controlled by the processor 18 is positioned on the lower portion of the support frame 22 and includes a drive chain 44 interconnecting a sprocket (not shown in detail) of the pellet transport chain 40. The stepper motor 42 provides accurate chain movement in timed sequence.

The pellet transport chain 40 includes laterally extending arms 46 extending toward the pellet support rolls. Each arm 46 includes a transport dog 48 fabricated from stainless steel wire with a hardened stainless steel flattened end braised to the end of each wire and which extends upward between the two pellet support rolls 28, 29 when a pellet transport chain link is positioned in the upper course of the pellet transport chain 40. The transport dogs 48 are attached to every other link and positioned 0.75 inches apart from each other on the center. The transport dogs 48 can accommodate the longer pellets which can range up to 0.6 inches in length. To accommodate varying diameters for different pellets, it is preferred that the chain ride in a grooved oilite track which is adjustable for height over approximately a 0.10 inch range. The pellet transport chain tension can be maintained by a spring-loaded sprocket (not shown) at the driven end.

In the pellet feed area 13a a pellet is delivered between two adjacent spaced transport dogs 48 as the pellet transport chain 40 advances between the rotating pellet support rolls. At the pellet feed area 13a a vibratory box feeder 50 feeds nuclear fuel pellets onto a feed track 52. The feed track 52 extends downward at an angle to a position between the rolls 28, 29. The pellets are fed in a magazine type arrangement on the feed track 52 so that at each advancement of the pellet transport chain 40, the transport dogs 48 engage a pellet and push the pellet between the pellet support rolls. As illustrated in FIG. 3, the end portion of the feed track 52 extends from a location outside the housing 24, such as from a pellet grinder (not shown), and through the housing 24.

The pellet discharge area 13b includes a downwardly extending pellet discharge track 54 positioned at the end of the first and second pellet support rolls 28, 29. The track 54 extends downward through the housing 24 and is adjustable in inclination of fall by an adjustable brace 55 to accommodate pellets P of differing weights. Preferably the pellet discharge track 54 is made of stainless steel. A reject solenoid 56 connected to the processor 18 actuates a stainless steel "kicker" 58 to displace rejected pellets into a reject bin 60 upon a command from the processor 18. Rejected pellets slide on a reject pellet track 61 into the reject bin positioned at the side of the pellet discharge track 54 (FIG. 3).

As noted before, the line scan camera 16 is positioned at the pellet inspection station 14 and axially scans a pellet surface. The line scan camera 14 acquires a "slice" of a pellet image as the cylindrical pellets rotate. Acquisition of many slices of a pellet yields a complete map of a pellet's peripheral surface. A number of commercially available line scan cameras can be used in the present invention. A Fairchild CAM 1500R or a Fairchild CAM 1830 line scan camera has been found acceptable. Each camera has a single line of 2,048 sensor cells and includes a large format lens to accommodate the length of the camera sensor cells. Preferably the lens has a small focal length to image the fuel pellets at a close range while maintaining image linearity. The camera can be adjusted on the table 26 so that its line of vision is on the pellets supported on pellet support rolls 28, 29.

A fluorescent light source 62 illuminates the fuel pellets for inspection as the fuel pellets move along the path of travel. The fluorescent light source 62 is positioned above the pellet path of travel at the inspection station 14 (FIGS. 1-3). High frequency fluorescent light source drivers (about 60,000 Hertz) are available from Mercron that will power the normal fluorescent bulbs commonly driven by a 60 Hertz power source. High frequency fluorescent light drivers allow several cycles of illumination to be integrated by the line scan camera 16 during acquisition of a line image so that the illumination will be very uniform. The Mercron drivers have a photocell feedback circuit that monitors the average light output of the fluorescent bulb to automatically boost or reduce the drive current to maintain a constant light output. A single 24" T-12 VHO bulb is anticipated for use.

Figure 6:
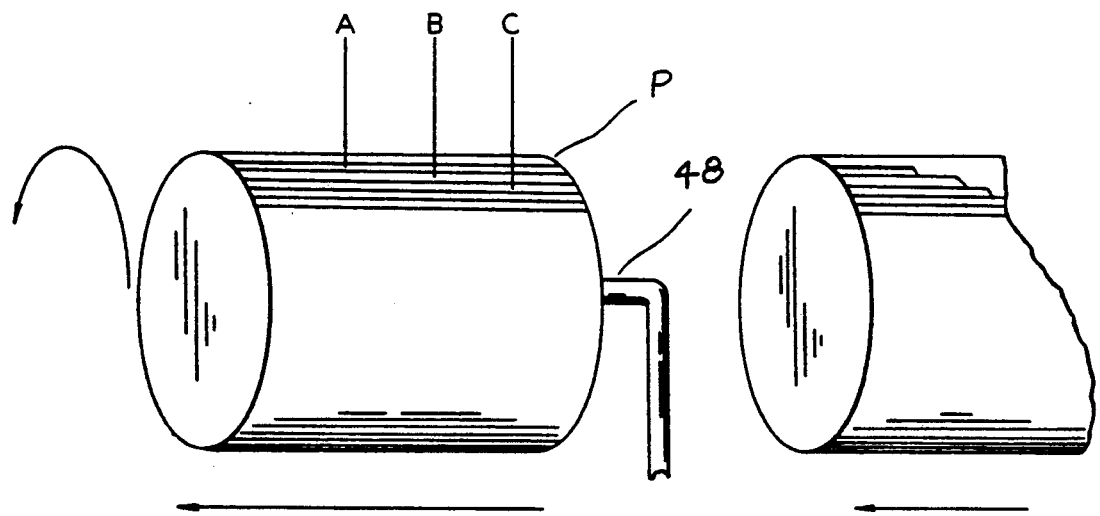
FIG. 6 is a schematic representation of optically sensing axially extending linear portions of pellets.

During operation, the line scan camera 16 optically senses the entire pellet surface by scanning axially extending linear portions of the peripheral surface of the pellet. The line camera continually senses pellets as they move into the camera line of view (FIG. 6) where successive scans of axially moving, rotating pellets are illustrated as scans A, B and C. The pellets are advanced at the rate of three to seven pellets per second, and preferably seven pellets per second, with a pellet revolution rate of one revolution per translation of five pellets. The rotation of the rolls 28, 29 is synchronized by the processor 18 with the advancement speed of the chain 40. As will be explained later in detail, the processor 18 receives signals from the line scan camera 16 representative of the surface of the pellet and compares the signals with a predetermined standard to identify groups of digital values having values greater or less than a predetermined standard.

The processor hardware is commercially available. High speed image processing hardware known as the Max Video family of modular VME boards provided by Data Cube, Inc. are preferred. This family of boards can provide image acquisition, image storage, pixel processing, neighborhood processing, look-up tables, histogramming, and feature extraction of an image display. Image data is transferred among the boards via the Max Video Bus which are digital cables operating at the rate of 10 million pixels per second with region-of-interest synchronized timing. Control of each Max Video board is performed by memory mapped registers over the Bus.

Figure 7:
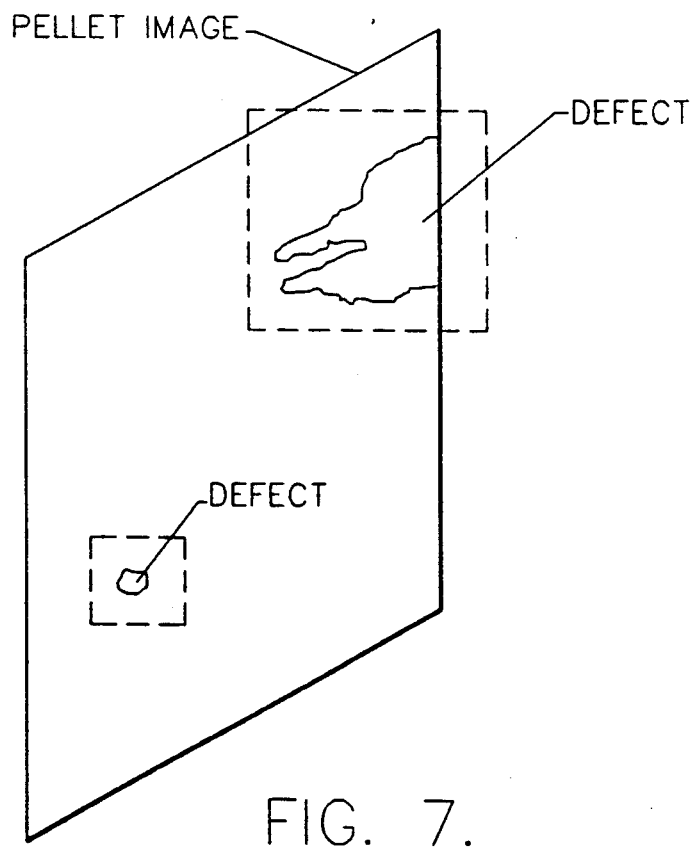
FIG. 7 is a schematic of the type of image which can be produced by the method and apparatus in accordance with the present invention and showing the representation of a defect of the pellet.

The other commercially available hardware used for identifying groups of digital values representative of adjacent locations on the surface of the pellet having values greater or less than the predetermined standard includes an APA-512 board (Area Parameter Accelerator for 512×485 images). This type of board is available from Vision Security, Inc. and is compatible with Max Video Bus specifications for Data Cube, Inc. high speed image processing hardware. Because of the speed limitations on the APA-512 board, the maximum vertical dimension is 460 lines. In operation, the line scan images of rotating pellets are acquired and stored which results in an image where the length of the pellet is represented horizontally and the circumference of the pellet is represented vertically. Because the pellet is moving axially, the image is skewed (FIG. 7). This image can be straightened. If ten extra line scans are acquired of a rotated pellet for allowing subsequent connectivity of potential flaws overlapping at the beginning and end of a single revolution of the pellet, the maximum number of line scans for a single revolution of the pellet is 450. If the maximum diameter of a pellet is 0.4 inch, then the minimum representation of a pixel will be 2.8 mils.

With a resolution of 2.8 mils per pixel, the maximum pellet length of 0.6 (plus or minus 0.50) inches will require 233 horizontal pixels to maintain a 1:1 pixel aspect ratio. This can result in approximately 450 vertical pixels by 233 horizontal pixels to obtain a result of approximately 105,000 total pixels per pellet image. Using the commercially available Max Video boards and Max Bus pixel processing pipelines, which have transfer rates of ten million pixels per second, there are no speed processing problems. One hundred and forty-three milliseconds per pellet is allowed by the maximum translational rate of seven pellets per second.

Because the pellets are spaced 0.75 inch on center, i.e., the transport dogs 48 being spaced 0.75 inch from each other on the pellet transport chain 40, a resolution of 2.8 mils per pixel will require 268 pixels assigned for each pellet in the field-of-view of the line scan camera. When a pellet makes one revolution per translation of five pellets, the field-of-view will be set for six pellets in order for the full length of the pellet to be digitized at each point through a complete rotation. A total of 6 times 268, or 1,608 pixels per field-of-view is necessary. Thus line scan camera having 2,048 sensor cells is sufficient. A maximum pellet translational rate of seven pellets per second, a minimum number of one pellet revolution per translation of five pellets, and a maximum pellet circumference of 0.6 inch times pi, or around 1.9 inches, and a minimum pixel resolution of 2.8 mils, together yield a maximum line scan rate of 943 lines per second or a minimum exposure interval of 1.061 millisecond per line scan. Operating a 2,048 element line scan camera at the maximum rate of 943 lines per second requires a pixel transfer rate on the order of about two million pixels per second. This transfer rate is well within the capability of the above described desired commercially available hardware.

METHOD OF OPERATION

Figure 4:
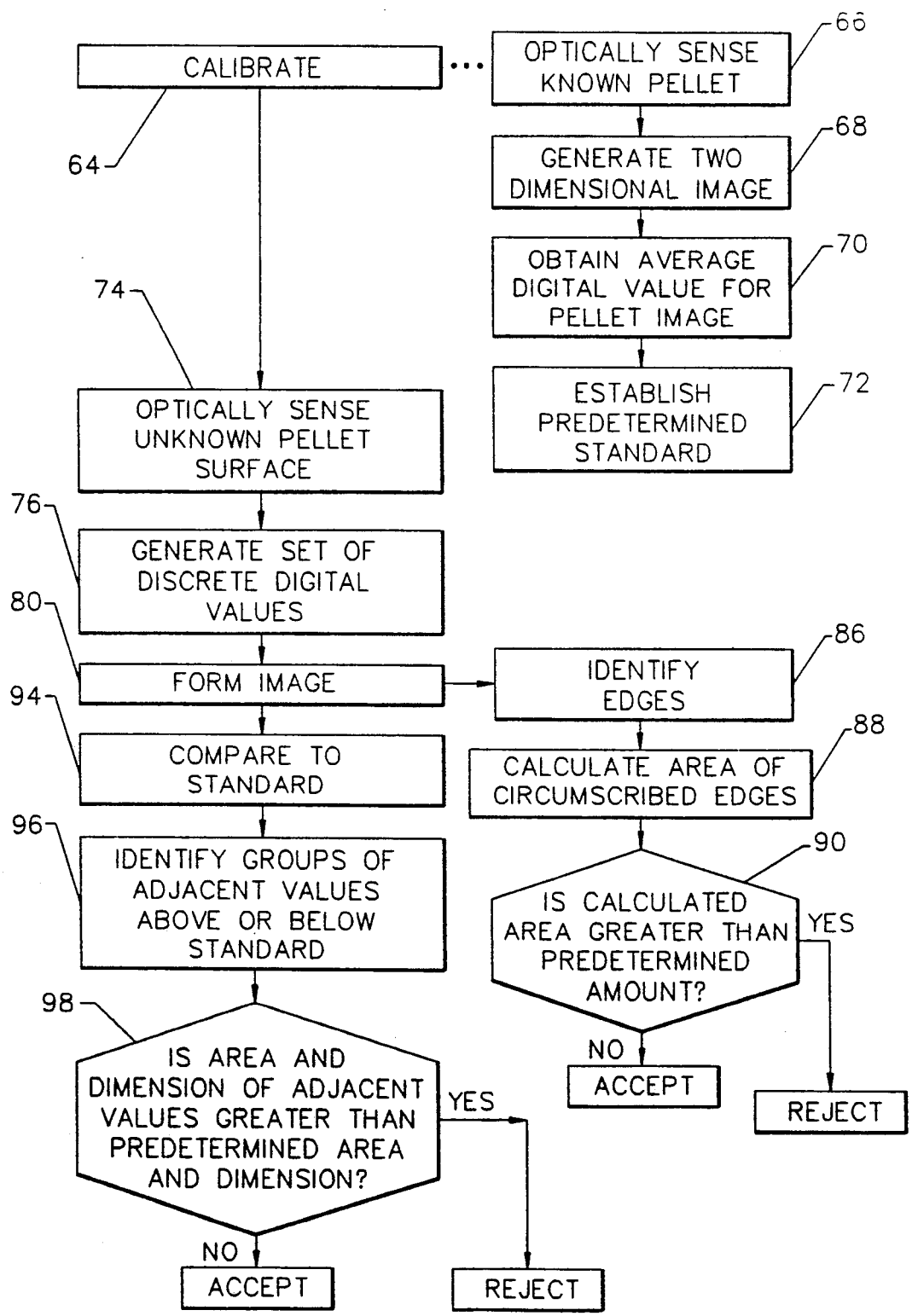
FIG. 4 is a flow chart representing the method for inspecting pellets for surface defects in accordance with the present invention.

The system is first calibrated with a known pellet as indicated in block 64 of the flow chart of FIG. 4. In accordance with the calibration procedure, the peripheral surface of a known pellet is optically sensed at block 66. A two dimensional digital image having a two dimensional array of digital values representative of the optically sensed surface of the known pellet is generated at block 68. An average value or video gray level over the entire pellet surface is determined at block 70. The predetermined standard is established from this average video gray level at block 72. The predetermined standard can be the range of values corresponding to the acceptable average video gray level of the known, acceptable pellet. The lower value in this range defines a lower threshold which is set darker on the video level. Later, valves below that threshold will be processed as a possible crack or chip defects which correspond to the dark areas such as cracks, tend to absorb more light than the surrounding peripheral pellet surface and are thus darker than the average gray level of the known, good pellet. The higher values in this range define an upper threshold which is lighter in video gray level. Values higher than this threshold will be processed as possible metal inclusions which tend to reflect light more than the surrounding peripheral surface and are lighter than the average gray level of the known, good pellet. Additionally, the system can be calibrated with more than one known good pellet, such as ten (10) pellets, and the average value obtained based on the average of those values.

After calibration, unknown fuel pellets are fed through the pellet feed area 13a to the pellet support rolls 28, 29. The stepper roll drive motors 32, 34, 42 controlling the rotation of the pellet support rolls 28, 29 and the advancement of the pellet transport chain 40 are operated by the processor 18 so that pellets are advanced at the preferred rate of seven pellets per second. The pellet support rolls 28, 29 rotate so that a pellet rotates once per translation of five pellets. Seven pellets are advanced per second and are spaced 0.75 inch on center as noted before. Thus, when the pellet transport chain 40 is moving at seven pellets per second and the pellet rotates once per translation of five pellets, the total time the pellet is within the line scan camera field of view is five-sevenths of a second or 712 milliseconds.

The line scan camera 16 acquires "slices" i.e., linear portions of the cylindrical pellet as it rotates as indicated in block 74 of FIG. 4. A set of discrete digital values representative of the optically sensed linear portions is generated at block 76. The entire peripheral pellet surface is acquired as a set of digital values to yield a complete "surface map" of the pellet's circumferential surface as indicated at block 80 and an image can be formed. Because the pellets translate the line scan camera field-of-view, on a monitor the image of the pellet surface will appear diagonally skewed. The processor 18 software can straighten the image, if desired.

The timing aspects of the image processing system have three variables, i.e., the pellet rotation speed, the size of the pellets to be inspected, and the translational speed of each pellet. As noted before, the time required to acquire an image of a completely rotated pellet is the number of pellets of travel per single revolution of a pellet divided by the number of pellets per second in movement. Thus, at the preferred pellet translation rate of seven pellets per second with a pellet rotation rate of one rotation per translation of five pellets, the total time the pellet is within the camera field of view is 714 milliseconds. However, a pellet image is ready for processing at the same rate as the translation speed, seven times a second, or 143 milliseconds.

The pixels containing the image of a completely rotated pellet are known to be within certain bounds and the pellet pixels (including surrounding background pixels) are transferred in rectangular fashion by selection of region of interest timing constraints. The data travels three parallel pipelines for processing of the pixel information on the hardware boards. It is understood that the processing of information can occur serially; however, speed is obtained by the parallel processing. Two of the parallel processing pipelines are illustrated in FIG. 4 and shown as beginning at block 80 and continuing across to block 86 for one pipeline and downward from block 80 to block 94 for the other pipeline. The pixels containing the image of a completely rotated pellet are stored in skewed fashion, and the image can be straightened if desired at block 82.

Figure 5:
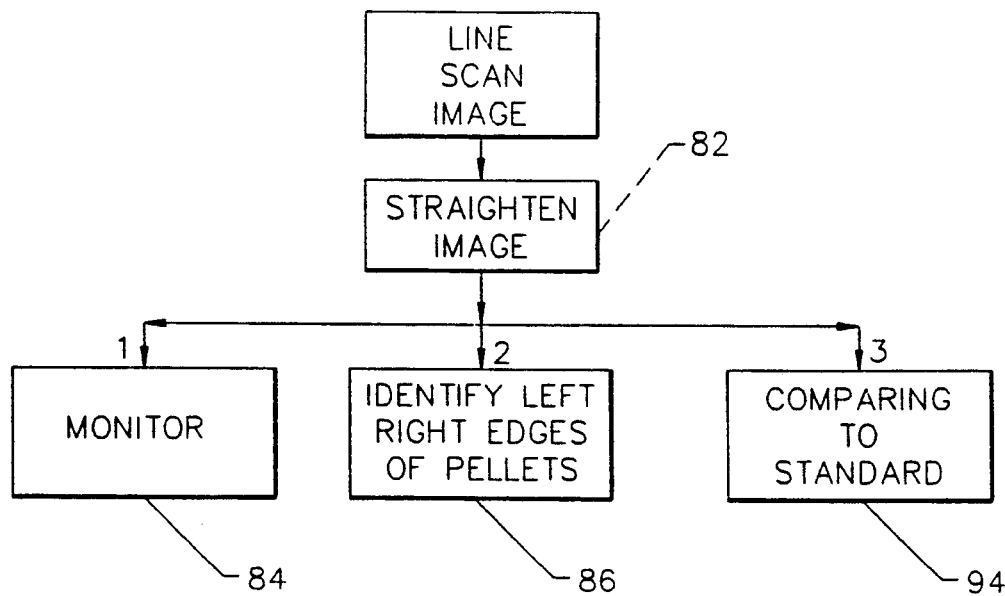
FIG. 5 is a flow chart representing pixel processing pipelines as processed on the hardware.

In the first pipeline numbered one in FIG. 5, the pixels are stored for subsequent display on a video display monitor 84. In the second processing pipeline, numbered 2, a binary image of the pellet is obtained by thresholding above the background video level to determine the coordinates of left and right edge of the pellet as noted at block 86 in FIGS. 4 and 5. The pixels are stored and the exact dimensions of the pellet calculated. For left and right edge points, a vertical line is fit through the coordinates and the horizontal coordinate of left and right edge lines establish region of interest coordinates for extracting a pellet image, which used in the third pipeline. Edge detection is important for later identification of a pellet. When a pellet is determined to be positioned on the pellet transport chain 40, its position relative to the pellet discharge area and reject means is known because the processor 18 controls advancement of the chain 40 and actively tracks movement from the field-of-view of the line scan camera 16 to the pellet discharge area and into a position adjacent the kicker 58. Once the left and right edges are determined, the area circumscribed by the edges of the pellet is determined in block 88 of FIG. 4. This area is compared with a predetermined amount in block 90, and if it does exceed a predetermined amount, the pellet is rejected. Too great a circumscribed area indicates the presence of edge cracks, chips and other unacceptable defects. The unacceptable limits of the area are established beforehand and can be based on the fuel pellet end-use requirements. Too great a circumscribed area correspond to an edge having defects such as chips.

In the third parallel processing pipeline, the value of each pixel is compared with the predetermined standard in block 94 of FIGS. 4 and 5. Those values above or below the predetermined standard are processed as "hits." From the acquired pellet image, the calibrated average pellet gray level is subtracted from each pixel and stored as a value. Groups of adjacent values above or below the standard are identified in block 96 and the dimensions, including the area of adjacent values are compared with predetermined areas and dimensions in Block 98. Adjacent values less than the predetermined standard are processed together and the area determined corresponding to the area of a crack, chip or fissure. When the calculated area exceeds a predetermined area corresponding to an unacceptable defect size, the pellet is rejected. Later, as the pellet is moved, a reject signal is automatically generated to the reject solenoid when the pellet is positioned adjacent the kicker 58 which is activated to push the pellet off the track into the reject bin 60. Additionally, for hairline cracks, if the length of a crack, i.e., the linear dimension of adjacent values, is longer than a predetermined dimension, the pellet is rejected because the hairline crack is longer than desired. A similar analysis occurs with those adjacent values above the predetermined standard corresponding to the lighter areas, i.e., metal inclusions. When the area of adjacent values exceeds a predetermined area the pellet is rejected as before.

During processing, the image of the last pellet that exited the camera field-of-view is shown (preferably straightened) on the video display monitor. Overlay graphics can be used to report the current rejection percentages over the past minute, hour, shift and month. The image will remain on the display for about 143 milliseconds (at the maximum translational rate of seven pellets per second) until an interrupt occurs which signals that the next pellet has exited the camera field-of-view. Line scan images are continuously acquired.

Depending on the fuel requirements of a particular customer, the predetermined standards, dimensions and areas are varied as needed. The following criteria are an example of acceptable ranges which can be used for the rejection of nuclear fuel pellets. Circumferential cracks, i.e. cracks parallel to the pellet end, are rejected if the width exceeds 0.006 inches and have a length over 0.020 inches. Longitudinal cracks perpendicular to the pellet end are unacceptable if the width exceeds 0.006 inches and the length exceeds 0.100 inches. Thumb nail cracks which extend to the pellet end and having a width exceeding 0.006 inches in length and exceeding 0.015 inches are unacceptable. If the pellet surface contains a pit or chip greater than 0.0005 square inch, the pellet should be rejected.

In the drawings and specification, there has been set forth the preferred embodiment of the invention, and while specific terms are employed, they are used in a generic and descriptive sense only and not for purposes of limitation.

We claim:

1. A method of inspecting cylindrically configured pellets for surface defects comprising the steps of
   optically sensing the entire peripheral surface of a pellet as a series of sets of discrete digital values representative of different axially extending linear portions of the peripheral surface of a pellet,
   generating a set of discrete digital values representative of the optically sensed portions of the pellet surface,
   forming an image of the entire peripheral surface of the pellet from said series of sets of discrete digital values,
   identifying the digital values corresponding to the edges of the pellet,
   calculating the area circumscribed by the edges of the pellet and rejecting the pellet is the calculated value is greater than a predetermined amount.

2. The method according to claim 1 including the further step of comparing the set of digital values to a predetermined standard to identify groups of digital values representative of adjacent locations on the surface of the pellet having values greater or less than the predetermined standard.

3. The method according to claim 2 including the step of rejecting a pellet when a compared set of digital values is greater or less than the predetermined standard.

4. The method according to claim 2 including the step of rotating the pellet and optically sensing in timed sequence the series of different axially extending portions of each pellet as it rotates to obtain said series of sets of discrete digital values.

5. The method according to claim 2 including the step of moving the pellet axially through an inspection station while optically sensing the peripheral surface.

6. The method according to claim 2 wherein said predetermined standard comprises a range of digital values having upper and lower limits defining upper and lower thresholds.

7. The method according to claim 2 including the steps of calculating the area of adjacent digital values which have a value less than the predetermined standard, and rejecting a pellet when the calculated area is greater than a predetermined area.

8. The method according to claim 2 including the step of calculating the linear dimension of adjacent digital values which have a value less than the predetermined standard and rejecting a pellet when the linear dimension is greater than a predetermined dimension.

9. The method according to claim 2 including the step of calculating the area of adjacent digital values which have a value greater than the predetermined standard and rejecting a pellet when the area is greater than a predetermined area.

10. A method of inspecting cylindrically configured pellets for surface defects comprising the steps of
    generating a two-dimensional digital image having a two-dimensional array of digital values representative of the peripheral surface of a known pellet,
    determining an average value for the array of digital values in the two-dimensional digital image,
    determining a threshold standard from the average value,
    generating a set of discrete digital values representative of an unknown pellet surface,
    comparing the set of digital values to the threshold standard,
    identifying groups of digital values representative of adjacent locations on the surface of the pellet having values greater or less than the threshold standard, and
    rejecting an unknown pellet when the number of digital values having a value greater or less than the threshold standard exceeds a certain number,
    while also identifying the digital values corresponding to the edges of the unknown pellet, calculating the area circumscribed by the edges of the pellet and rejecting the pellet if the calculated value is greater than a predetermined amount.

11. The method according to claim 10 including the step of rotating the pellet and optically sensing in timed sequence the series of different axially extending portions of each unknown pellet as it rotated to obtain said series of sets of discrete digital values.

12. The method of according to claim 11 including the step of moving the unknown pellet axially through an inspection station while optically sensing the peripheral surface.

13. The method according to claim 10 including the steps of calculating the area of adjacent digital values which have a value less than the threshold standard, and rejecting an unknown pellet when the calculated area is greater than a predetermined area.

14. The method according to claim 10 wherein said threshold standard comprises a range of digital values having upper and lower limits.

15. The method according to claim 10 including the step of calculating the linear dimension of adjacent digital values which have a value less than the threshold standard and rejecting a pellet when the linear dimension is greater than a predetermined dimension.

16. An apparatus for inspecting cylindrically configured pellets for surface defects comprising
    means for axially transporting a pellet along a path of travel through an inspecting station while rotating the pellet along its longitudinal axis, said transporting means including first and second horizontally positioned substantially parallel and longitudinally extending pellet support rolls, said rolls being transversely spaced a distance from each other less than the diameter of a pellet to be transferred, drive means connected to said pellet support rolls for rotating each of said rolls to impart a net rotation to the pellets, means positioned between the spaced rolls for engaging a pellet and moving the pellet between the spaced pellet support rolls, said moving means further including an endless loop pellet transport chain positioned adjacent and below one of said pellet support rolls, said pellet transport chain including a plurality of spaced, laterally extending arms having dogs thereon, said endless loop pellet transport chain being positioned so that during movement of said chain, said dogs are moved longitudinally between said rolls for engaging and moving a pellet supported thereon, line scan camera means positioned at said inspection station for scanning axially the pellet surface, control means comprising a) receiving means for receiving signals received from said line scan camera means to a predetermined standard and identifying groups of digital values representative of adjacent locations on the surface of the pellet having values greater or less than the predetermined standard, and reject means responsive to said control means for rejecting defective pellets.

17. The apparatus as claimed in claim 16 wherein each of said pellet support rolls is rotated upward and outward from each other.

18. The apparatus according to claim 16 including feed means for delivering a pellet onto said pellet support rolls and between two adjacent spaced dogs.

19. The apparatus according to claim 16 said reject means comprises means for moving a pellet transversely out of the pellet path of travel when a pellet is determined defective.

20. The apparatus according to claim 16 including a pellet discharge station having a downwardly extending chute positioned adjacent the end of said pellet support rolls for receiving a pellet delivered from said rolls, and said reject means comprises means positioned adjacent said chute for pushing a pellet transversely from off said chute.

21. A pellet transfer apparatus for transporting pellets axially along a predetermined path of travel from a pellet feed area to a pellet discharge area comprising first and second horizontally positioned substantially parallel and longitudinally extending pellet support rolls, said rolls being transversely spaced a distance from each other less than the diameter of a pellet to be transferred, said pellet support rolls defining at least a portion of the predetermined path of travel, means positioned between the spaced rolls for engaging a pellet and moving a pellet between the spaced pellet support rolls along said path of travel, and drive means connected to said pellet support rolls for rotating said pellet support rolls upward and outward from each other to aid in preventing chips or other material dislodged from the pellet from being forced downward between the rolls and into other components of the pellet transport apparatus, and wherein one of said pellet support rolls is rotated faster than the other pellet support roll to impart a net rotation to the pellet supported on the pellet support rolls.

22. The apparatus as claimed in claim 21 wherein said faster rotating pellet support roll is rotated at twice the speed of said other pellet support roll.

23. The apparatus according to claim 21 wherein said moving means positioned between said transversely spaced pellet support rolls for engaging and moving a pellet includes a longitudinally extending endless loop pellet transport chain positioned adjacent and below one of said pellet support rolls, said pellet transport chain including a plurality of spaced, laterally extending arms having dogs thereon, said endless loop pellet transport chain being positioned so that during movement of said chain, said dogs are moved between said rolls and longitudinally therebetween for engaging and moving a pellet supported thereon.

24. The apparatus according to claim 23 including feed means positioned at said pellet feed area for delivering a pellet onto said pellet support rolls and between two adjacent spaced dogs.

25. The apparatus according to claim 23 including reject means positioned at said pellet discharge area for moving a pellet transversely out of the pellet path of travel.

26. The apparatus according to claim 23 wherein said pellet discharge area includes a downwardly extending chute having a pellet entrance positioned adjacent the end of said pellet support rolls for receiving a pellet delivered from said rolls, and said reject means comprises means positioned adjacent said chute for pushing a pellet from off said chute.

* * * * *